United States Patent [19]

Schmidt et al.

[11] Patent Number: 5,015,749

[45] Date of Patent: May 14, 1991

[54] PREPARATION OF POLYHYDROCARBYL-ALUMINOXANES

[75] Inventors: Gregory F. Schmidt; Dennis A. Hucul; Richard E. Campbell, Jr., all of Midland, Mich.

[73] Assignee: The Dow Chemical Company, Midland, Mich.

[21] Appl. No.: 405,118

[22] Filed: Sep. 7, 1989

Related U.S. Application Data

[63] Continuation of Ser. No. 91,566, Aug. 31, 1987, abandoned.

[51] Int. Cl.$^5$ .............................................. C07F 5/06
[52] U.S. Cl. .................................................. 556/179
[58] Field of Search ......................................... 556/179

[56] References Cited

U.S. PATENT DOCUMENTS

| | | | |
|---|---|---|---|
| 3,454,615 | 7/1969 | Tani et al. | 556/179 |
| 4,544,762 | 10/1985 | Kaminsky et al. | 556/179 |
| 4,665,208 | 5/1987 | Welbor et al. | 556/179 |

FOREIGN PATENT DOCUMENTS 0208561  7/1986  European Pat. Off. ...... 556/179 UX

*Primary Examiner*—Paul F. Shaver
*Attorney, Agent, or Firm*—Douglas N. Deline

[57] ABSTRACT

An improved process for the preparation of aluminoxanes comprising contacting an aluminoxane precursor such as a hydrocarbyl substituted aluminum compound with a porous organic or inorganic aqueous imbiber material containing water sorbed or imbibed therein.

10 Claims, No Drawings

PREPARATION OF POLYHYDROCARBYL-ALUMINOXANES

This is a continuation of application Ser. No. 091,566 filed Aug. 31, 1987.

BACKGROUND OF THE INVENTION

The present invention relates to the preparation of aluminoxanes, also known as polyhydrocarbylaluminoxanes. A preferred composition is polymethylaluminoxane. Polyhydrocarbylaluminoxanes are previously well-known in the art and are used as a component in the preparation of high activity homogenous Ziegler catalysts.

In Kaminsky, et. al. U.S. Pat. No. 4,544,762 there is disclosed a preparation of aluminoxanes employing the reaction between a hydrated aluminum salt and aluminum alkyls. Particularily desirable was the reaction between hydrated aluminum sulfate and aluminum trimethyl. The reaction is conducted in an inert solvent. For the teachings contained therein, the above identified patent is herein incorporated in its entirety by reference thereto.

EP 208,561 A2 discloses a similar process utilizing hydrated iron, magnesium, zinc and sodium salts. In each prior art process, the initial reagent was a trihydrocarbylaluminum compound. Despite advances in the art in the preparation of aluminoxanes, previously known processes have resulted in excessively long reaction times and an inability to recycle the metal salt employed therein. Moreover, such processes required tedious comminution of the hydrated salt in order to obtain selective control of the rate at which water is released to the reaction and thus control of the molecular weight and structure of the resulting aluminoxane compound.

It would be desirable if there were provided an improved process for the preparation of polyhydrocarbylaluminoxanes that would enable the skilled artisan to obtain improved efficiency.

In addition, it would be desirable to provide an improved process that would permit the facile regeneration of the hydrating agent.

It would also be desirable if there were provided a method allowing greater control of the release of water to the reaction mixture and an ability to utilize differing reactants, particularly lower grade or oligomeric aluminoxane materials such as are presently commercially available and to produce higher molecular weight materials therefrom.

Finally, it would be desirable if there were provided a continuous process for preparation of aluminoxane.

SUMMARY OF THE INVENTION

According to the present invention there is now provided an improved process for the preparation of polyhydrocarbylaluminoxanes comprising contacting under reaction conditions that are conducive to the preparation of polyhydrocarbylaluminoxanes, a polyhydrocarbylaluminoxane precursor compound and a porous organic or inorganic aqueous imbiber material containing water imbibed or sorbed therein.

Because of the greater efficiency with which water is supplied to the hydration reaction by means of the above described porous materials, the present process attains improved production economies and greater control over the resulting aluminoxane structure. Moreover, improved rates of polyhydrocarbylaluminoxane preparation are also obtained. In addition, the source of water for hydration of the precursor material may be readily regenerated by suitable techniques. Accordingly, the present process allows for recycle of such imbiber material in an economic and facile manner. Such recycling permits the process to be operated in a semi-continuous or batch manner wherein the reactants and porous imbiber material are contacted, the imbiber material is separated, then regenerated, and the procedure repeated. The process may also be operated in a truly continuous manner, wherein reagents are continuously added to a reactor operating under homogeneous, steady state conditions or in a plug flow mode, the porous imbiber material is separated and regenerated, and the regenerated porous material is continuously recharged to the process.

Finally, utilizing the present invention, it is possible to upgrade lower molecular weight polyhydrocarbylaluminoxanes or other precursor materials to obtain higher molecular weight forms thereof or differing molecular structures thereof.

DETAILED DESCRIPTION OF THE INVENTION

By the term "polyhydrocarbylaluminoxane precursor" is meant any hydrocarbyl substituted aluminum compound, which may be monomeric, oligomeric or polymeric, optionally containing inert substituents. Examples include trihydrocarbylaluminum compounds as well as aluminoxanes having differing molecular weight or structure from that desired according to the present invention, and mixtures thereof. Preferred polyhydrocarbylaluminoxane precursors for use according to the present invention are trialkylaluminum compounds having from 1 to 4 carbons in each alkyl group. Particularly preferred is trimethylaluminum.

Suitable porous aqueous imbiber materials for use according to the present invention include the porous organic ion exchange resins, e.g. macroporous resins such as those available from The Dow Chemical Company under the trade name Dowex ® or from Rohm and Haas Company under the trade name Amberlite ®, etc. and porous inorganic materials such as silicas, silicates, aluminosilicates, aluminas and particulated carbons, such as acetylene black or other suitable porous carbon material. A particularly desirable porous aqueous imbiber material is porous, high surface area silica or alumina.

Preferred porous aqueous imbiber materials are compositions having an average pore diameter from about 15 to about 10,000 Angstroms, highly preferably from about 40 to about 2,000 Angstroms and most preferably from about 100 to about 1,000 Angstroms. In addition, it is highly desirable to employ such compositions having a total surface area from about 1 $M^2/g$ to about 1200 $M^2/g$. Preferably from about 5 $M^2/g$ to about 500 $M^2/g$. An especially preferred aqueous imbiber material is capable of regeneration to remove residual contaminants and to replace water consumed by the reaction. A suitable regeneration technique is to wash the used porous imbiber material with a suitable solvent to remove contaminants or to heat the material to a suitable temperature, e.g. calcine the material, and then to contact the material with water or an aqueous acid solution to replace consumed water.

In the process, the starting reactant is contacted with the porous aqueous imbiber material containing sorbed water in any suitable manner. In a preferred embodiment, the polyhydrocarbylaluminoxane precursor and aqueous imbiber material are combined in an inert liquid. Preferred inert liquids are $C_{6-12}$ aliphatic or aromatic hydrocarbons or mixtures thereof. Specific examples include toluene, hexane, heptane, decahydronaphthalene, etc. Most preferred diluents are those capable of forming a homogeneous solution of the resulting aluminoxane. One example is toluene. Another preferred inert liquid is a compound or a mixture of compounds at least one of which has a boiling point above that of the polyhydrocarbylaluminoxane precursor compound. Such a selection of diluents allows the operator to distill the resultant product mixture and remove residual amounts of low boiling precursor leaving the resulting aluminoxane in the inert liquid.

The polyhydrocarbylalumlinoxane precursor and porous aqueous imbiber material are contacted under an inert atmosphere such as nitrogen, argon, etc. at suitable reaction temperatures. Suitable temperatures are those from about $-100°$ C. to the reflux point of the reaction mixture, preferably from about $-20°$ C. to about $50°$ C. Where a trihydrocarbylaluminum compound is employed as the polyhydrocarbylaluminoxane precursor, it may be first dissolved or dispersed in an inert diluent and the porous aqueous imbiber material having water sorbed therein added thereto accompanied by mechanical stirring and optional heating or cooling. Alternatively, the trihydrocarbylaluminum reactant may be added to a suitable solution or suspension of the porous aqueous imbiber material. Care should be exercised to avoid excessive heat generation. Cooling techniques, the use of a low boiling refluxing solvent and the slow addition of the various reactants may all be employed.

Where it is desired to employ an existing form of aluminoxane as the precursor, a small quantity of a trihydrocarbylaluminum compound is also desirably present. The trihydrocarbylaluminum compound may be found already present in a minor concentration in aluminoxane prepared utilizing prior art techniques, or may be intentionally added thereto prior to the reaction.

The reaction is allowed to continue with stirring for a sufficient time to enable the desired degree of conversion of the polyhydrocarbylaluminoxane precursor. Suitable contacting times are on the order of several minutes to several hours.

The aluminoxane, which normally is in homogeneous solution, may be employed as is or may be recovered and dispersed or slurried in an inert diluent. The latter form is particularly desirable in the preparation of olefin polymers according to the well-known "slurry" process. The polyhydrocarbylaluminoxane product may be recovered by simply separating the porous aqueous imbiber material and devolatilizing the inert diluent.

The present process allows the preparation of polyhydrocarbylaluminoxanes in greater effeciency, purity and convenience than previously known processes. Moreover the present process results in greater control over the molecular weight and structure of the final product due the uniformity in which water is supplied to the reaction. It is this latter feature that permits the operator to employ previously produced aluminoxanes as precursor materials to form polyhydrocarbylaluminoxanes having altered molecular weight and-/or structure according to the present invention.

Having described the invention, the following example is provided as further illustrative and is not to be construed as limiting.

EXAMPLE 1

A reaction vessel was charged with nitrogen and then with 1,750 ml of purified toluene and 800 ml of a 2.0 Molar trimethylaluminum solution in toluene. The reaction mixture was cooled to $-78°$ C. and 58 grams of silica (Shell S980H-1.5) having a surface area of 87 $M^2/g$ and a volume average pore diameter of about 600 Angstroms which had been previously impregnated with 28.8 ml of water were added accompanied by stirring. After 30 minutes, the reaction mixture was allowed to warm to room temperature. Three and one half hours after the reaction was initiated, a heating mantle was fitted to the reactor and the reaction mixture heated to reflux and maintained at reflux for 90 minutes.

The resulting product mixture was then cooled to room temperature and the clear liquid solution decanted from the silica spheres. Volatile reaction products were removed by vacuum distillation. Yield of solid polymethylaluminoxane was 43.3 grams, 46% of theory.

EXAMPLE 2

The reaction conditions of Example 1 were substantially repeated utilizing 9.5 g. of high surface area alumina having a surface area of 15 $M^2/g$. and an average pore diameter of 1700 Angstroms (SCM-9X available from Rhone Poulenc). The alumina was impregnated with 4.75 g. of water.

The reaction was conducted in a solvent mixture comprising 200 ml. of hexane and 150 ml. of heptane containing 0.4 moles of trimethylaluminum as the aluminoxane precursor. The alumina spheres were added under nitrogen atmosphere with stirring at room temperature. After 18 hours reaction the aluminoxane was recovered. No gel formation was observed thereby indicating controlled release of water to the reaction.

What is claimed:

1. A process for the preparation of polyhydrocarbylaluminoxanes comprising contacting under reaction conditions that are conducive to the preparation of polyhydrocarbylaluminoxanes a polyhydrocarbylaluminoxane precursor and a porous organic or inorganic aqueous imbiber material having a pore size of from about 15 to about 10,000 Angstroms containing water imbibed or sorbed therein.

2. A process according to claim 1, wherein the polyhydrocarbylaluminoxane precursor is a hydrocarbyl substituted aluminum compound.

3. A process according to claim 1, wherein the polyhydrocarbylaluminoxane precursor is selected from the group consisting of trihydrocarbylaluminum compounds having from 1 to 12 carbons in each hydrocarbyl group and polyhydrocarbylaluminoxanes having a molecular weight or structure different from that prepared by the process.

4. A process according to claim 3, wherein the trihydrocarbylaluminum compound is trimethylaluminum.

5. A process according to claim 1, wherein the porous aqueous imbiber material is high surface area silica or alumina.

6. A process according to claim 1, wherein the porous aqueous imbiber material has a pore size of from about 40 to about 2,000 Angstroms.

7. A process according to claim 1, wherein the reaction is conducting in the presence of an inert diluent.

8. A process according to claim 7, wherein the inert diluent in toluene.

9. A continuous process according to claim 1, wherein after preparation of the polyhydrocarbylaluminoxane the porous aqueous imbiber material is recovered, regenerated and reused to prepare a polyhydrocarbylaluminoxane.

10. A continuous process for the preparation of polyhydrocarbylaluminoxanes comprising
   (a) contacting under reaction conditions that are conducive to the preparation of polyhydrocarbylaluminoxanes, a polyhydrocarbylaluminoxane precursor and a porous organic or inorganic aqueous imbiber material containing water imbibed or sorbed therein;
   (b) recovering the polyhydrocarbylaluminoxane and porous aqueous imbiber material;
   (c) regenerating the porous aqueous imbiber material; and
   (d) repeating steps (a), (b) and (c).

* * * * *